US006379342B1

(12) United States Patent
Levinson

(10) Patent No.: US 6,379,342 B1
(45) Date of Patent: Apr. 30, 2002

(54) AMPOULE FOR DISPENSING MEDICATION AND METHOD OF USE

(75) Inventor: Melvin Levinson, Miami, FL (US)

(73) Assignee: Scion International, Inc., Miami, FL (US)

( * ) Notice: Subject to any disclaimer, the term of this patent is extended or adjusted under 35 U.S.C. 154(b) by 0 days.

(21) Appl. No.: 09/285,134

(22) Filed: Apr. 2, 1999

(51) Int. Cl.[7] .............................................. A61M 35/00

(52) U.S. Cl. ....................... 604/310; 604/257; 222/212; 222/129; 222/1

(58) Field of Search ................................ 604/257, 132, 604/142, 153, 310, 316, 327; 222/81, 1, 129, 83, 207, 456, 83.5, 212, 420

(56) References Cited

U.S. PATENT DOCUMENTS

| | | | | | |
|---|---|---|---|---|---|
| 1,909,209 | A | * | 5/1933 | Miller | |
| 2,848,995 | A | | 8/1958 | Ryan | |
| 3,171,412 | A | | 3/1965 | Braun | |
| 3,760,805 | A | * | 9/1973 | Higuchi | 128/260 |
| 3,792,699 | A | * | 2/1974 | Tobin et al. | 128/2 W |
| 3,995,631 | A | * | 12/1976 | Higuchi et al. | 128/260 |
| 4,049,034 | A | | 9/1977 | Vcelka et al. | |
| 4,294,250 | A | | 10/1981 | Dennehay | |
| 4,303,067 | A | | 12/1981 | Connolly et al. | |
| 4,482,585 | A | * | 11/1984 | Ohodaira et al. | 428/35 |
| 4,838,875 | A | | 6/1989 | Somor | |
| 5,006,118 | A | * | 4/1991 | Yule | 604/408 |
| 5,219,337 | A | | 6/1993 | Takata et al. | |
| 5,266,266 | A | * | 11/1993 | Nason | 422/58 |
| 5,403,289 | A | * | 4/1995 | Berrebi et al. | 604/232 |
| 5,405,333 | A | | 4/1995 | Richmond | |
| 5,624,057 | A | * | 4/1997 | Lifshey | 222/212 |
| 5,738,657 | A | * | 4/1998 | Bryant | 604/145 |

* cited by examiner

*Primary Examiner*—Richard K. Seidel
*Assistant Examiner*—Kevin C. Sirmons
(74) *Attorney, Agent, or Firm*—Robert M. Schwartz

(57) ABSTRACT

An ampoule which has been designed to contain sterile medicinal fluids of various types and doses in a measured dose fashion, which allows direct administration via linkage to standardized existing indwelling catheters, tubing and even hypodermic needle hubs by virtue of a contained Luer Lock fitting. The invention eliminates the need to draw up fluids into intermediary devices such as needles and syringes or other injection devices, thus minimizing costs and enhancing safety and convenience. The ampoule, by virtue of finger pressure on its flexible structure, allows complete administration directly into the body or its structures. The contents of the ampoule are protected and the sterility of contents and linkage mechanism is protected by a cover which occludes the opening into the ampoule until use. The ampoule also allows direct administration by connection of its Luer Lock fitting to standard hypodermic needles and hubs for injection into or through body structures.

11 Claims, 2 Drawing Sheets

AMPOULE FOR DISPENSING MEDICATION AND METHOD OF USE

BACKGROUND OF THE INVENTION

FIELD OF THE INVENTION

The ampoule of the present invention is used for medical purposes to dispense a predetermined dosage of medicine through a contained Luer Lock connector into a structure having a standard Luer Lock connector.

SUMMARY OF THE INVENTION

Generally, the invention is a flexible single-use ampoule, preferably having an opening with a Luer Lock connector fitting, which can be directly attached to indwelling venous lines for infusion of a sterile medical fluid of various types and doses in a measured dose fashion. The fitting being a type well known in the medical industry e.g. a Luer Lock TM. The contents therein, a medicinal fluid e.g. heparin, can be squeezed into a venous line. The quantity of fluid would be a premeasured dosage for a specific application, e.g. approximately 2 cc or less or even 3 to 5 cc of fluid depending on the specific application dosage requirements.

The ampoule allows direct administration via linkage to standardized existing indwelling catheters, tubing and even hypodermic needle hubs by virtue of a contained Luer Lock fitting. The invention eliminates the need to draw up fluids into intermediary devices such as needles and syringes or other injection devices, thus minimizing costs and enhancing safety and convenience.

The ampoule, by virtue of finger pressure on its flexible structure, allows complete administration directly into the body or its structures. The contents of the ampoule are protected and the sterility of contents and linkage mechanism is protected by a cover which occludes the opening into the ampoule until use. The ampoule also allows direct administration by connection of its Luer Lock fitting to standard hypodermic needles and hubs for injection into or through body structures.

The ampoule may be filled from the end opposite the opening with the Luer Lock, where it is folded and sealed on its edge after such filling. The opening end would have a sterile twist off cap formed integrally therein. Since insertion of the fluid from the ampoule is directly into the venous line, an object of the invention is to eliminate the need of using a needle or syringe to transfer the fluid from a container to the indwelling line. Another object is for the twist-off cap to easily open the ampoule, and also keep the contents of the ampoule and the Luer Lock sterile. Yet another object of the invention is to improve dosage control of the amount of dispensed medicine to yield lower costs and to increase accuracy of the dispensing of medicine.

BRIEF DESCRIPTION OF THE DRAWINGS

In the drawings that form part of the description of a preferred embodiment of this invention and wherein like numbers refer to like structural elements.

DESCRIPTION OF THE PREFERRED EMBODIMENT

Figure 1:
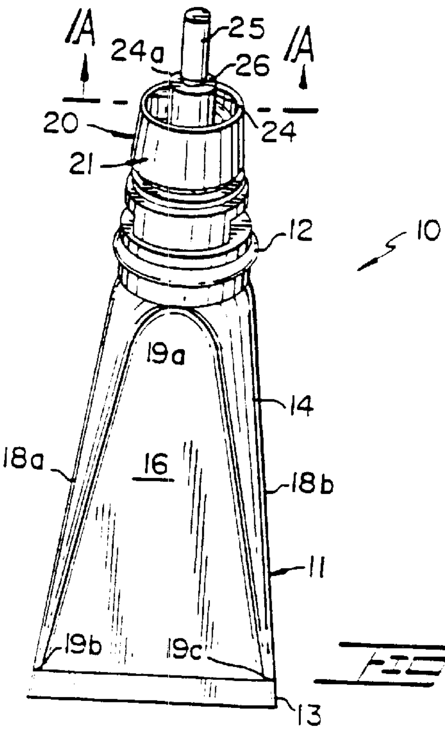
FIG. 1 is a perspective view of the ampoule of this invention.

Referring to FIG. 1, ampoule 10 is a liquid container body 11, for storage of preferably a medicinal fluid or other fluid. The container body 11 is of a generally cylindrical shape with a first end 12 that is open and which is of a circular cross-section, and, an opposite base second end 13 that is closed and which is of a rectangular cross-section, having a very narrow width and a relatively long length. Second end 13 is folded over on itself to form a permanent closure on the base of said container body 11.

Said container body 11 has opposed first 14 and second 15 sides, each said side having substantially identical indentations 16 and 17, respectively. Ampoule 10 also has opposed edges **18*a* and 18*b*, separated by a greater distance at second end 13 and by a lesser distance at first end 12. Said indentations 16 and 17 form a curved indentation having a curve top 19*a* at or near first end 12 and curve ends 19*b* and 19*c* of said curved indentation at opposed sides of said second end 13. Said curved indentation increasing in depth from top 19*a* to ends 19*b* and 19*c*.**

Figure 7:
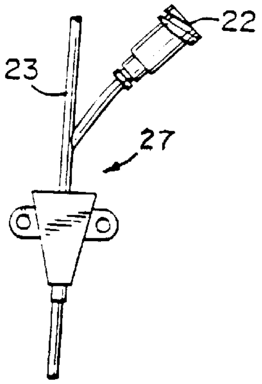
FIG. 7 shows a portion of an indwelling venous line with a branched venous line having a Luer Lock fitting to receive the Luer Lock fitting of the ampoule of the present invention.
Figure 2:
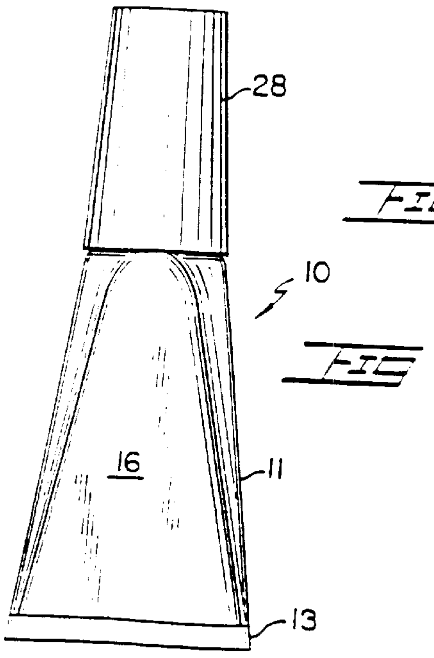
FIG. 2 is a front view of the ampoule of this invention with a cap.
Figure 3:
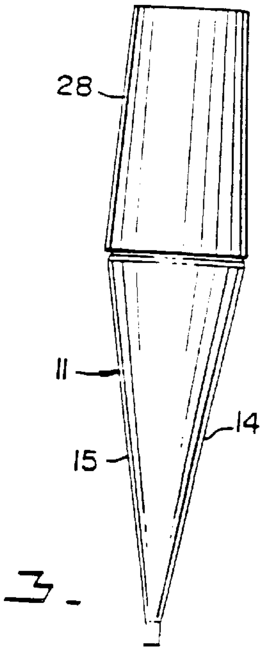
FIG. 3 is a side view of the ampoule of this invention with a cap.

Ampoule 10 includes a tip portion 20, that is preferably either attached to container body 11 or that is formed integrally with said container body 11. Tip portion 20 is constructed and arranged to form a hub, one-half of a standard Luer Lock assembly 21 compatible with a medical standard Luer Lock. As known in the art, almost all syringes, IV catheters, IV tubing connectors, and blood-tube connectors have either a male or female Luer connector. Each Luer connector has a round tapered mating surface. Luer connectors are connected by placing a male Luer connection 21 with a complimentary female Luer connector 22 (FIG. 7). The male and female connectors are put together after alignment and engaging the male and female connector, with a half-twist which is relatively secure. Luer Locks connect two ends of an intravenous line 23. In this manner, ampoule 10 with its Luer Lock connector 21 will connect to a mating Luer Lock connector 22 to discharge medicinal fluid contained in container body 11, through an opening 24 in distal end **24*a* of Luer Lock 21, into a venous line 23 (FIG. 7**).

Post 25 hermetically seals opening 24 of distal end **24*a* of a Luer Lock 21, sealing the contents of container body 11 and keeping same sterile from outside contamination. Post 25 is breakable from distal end 24*a* and includes a neck portion 26 having a smaller diameter than the other portion of post 25. Neck 26 is secured by a frictional fit or is otherwise attached by adhesive means to opening 24 of distal end 24*a*. Post 25 and neck 26 are constructed and arranged to seal the open 24 at distal end 24*a* of Luer Lock 21, sealing the contents of container body 11. Neck 26 is designed to be easily breakable such that the contents of container body 11 can be easily released. Neck portion 26 has a narrower diameter than the rest of post 25 such that said post can easily be broken off to administer the fluids contained in ampoule 10**.

Figure 1A:
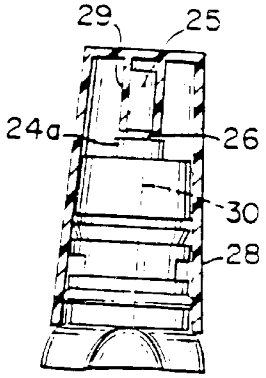
FIG. 1A is an enlarged view of a cross section along line 1A—1A of FIG. 1 of the top portion of the ampoule of FIG. 1 and including a cap portion.

Tip portion 20 can also be covered with a cap 28 constructed and arranged to cover and seal tip portion 20 to keep it clean and free of contamination. Said cap 28 is designed such that an internal slot 29 snugly fits over post 25, such that when it is desired to use ampoule 10, cap 28 is twisted to break off post 25 at neck 26. As seen in FIG. 1A, a channel 30 provides the passageway from container body 11 through tip portion 20 to opening 24 of distal end 24*a* of Luer Lock 21. When neck 26 is broken, channel 30, previously sealed by neck 26 at opening 24, is opened allowing the fluid contained in container body 11 to be squeezed out through channel 30. Luer Lock connectors 21 and 22 are designed with a channel therein such that fluids will pass from one structure to another.

Cap 28 is either integrally formed with tip portion 20 and connectively attached at post 25 or said cap 28 is placed on tip portion 20 to grasp post 25, at least with a friction fit connection, such that when cap 28 is turned, post 25 would turn and become twisted off, breaking at neck 26 to provide an opening of container body 11 at the distal end of channel 30. Cap 28 also acts as a sterile cover over the Luer Lock 21. Neck 26 is a groove or a score such that it is the weakest point, the break point, when cap 28 is twisted. In the friction fit, the neck 26 can then be sealed ultrasonically to opening 24*a,* or sealed by an adhesive to seal said opening 24*a*.

Figure 4:
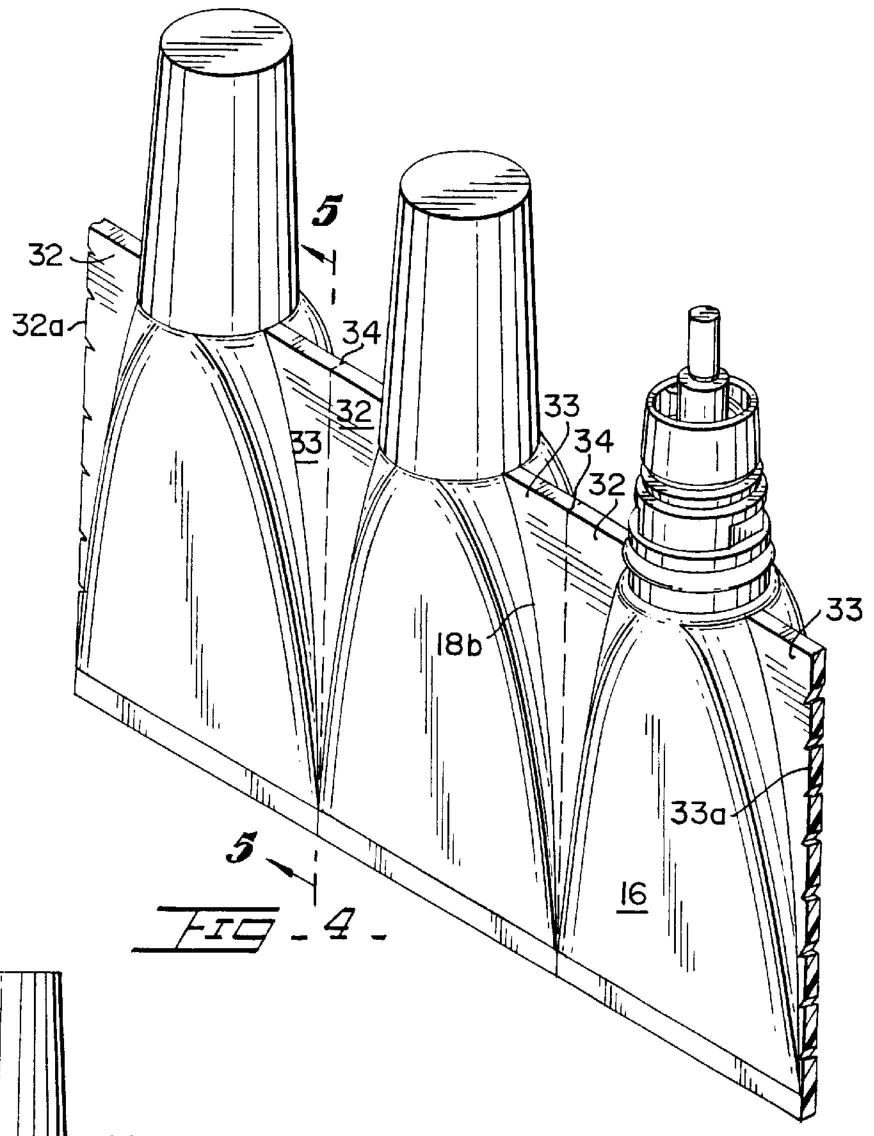
FIG. 4 is a perspective view of an alternative embodiment of three or more ampoules detachably connected and packaged edge to edge.
Figure 5:
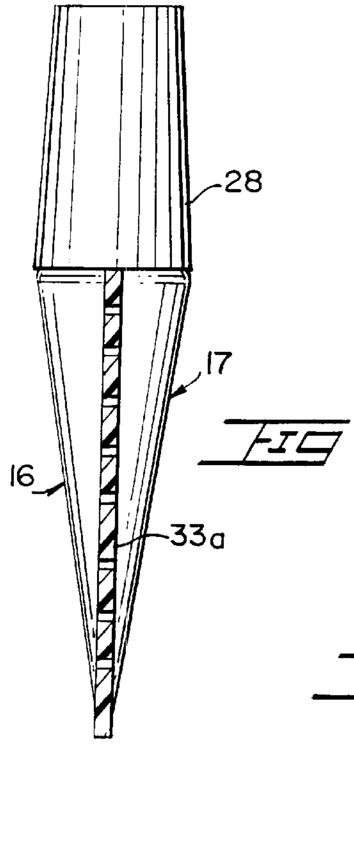
FIG. 5 is an end view along line 5—5 from FIG. 4.

An alternative embodiment is shown in FIG. 4, where two or more ampoules are connected edge-to-edge forming a series or pack of ampoules that may extend to multiple ampoules in a pack, e.g. 3, 4, 5, 6, etc., ampoules wide. In this multiple pack arrangement, ampoule 10 is substantially the same operationally as heretofore described. However, edges 18*a* and 18*b* extend laterally to form a pair of opposed flat ear portions 32 and 33 that have opposed parallel edges 32*a* and 33*a,* such that in a multiple ampoule package as shown in FIG. 4, an edge 32*a* of a first ampoule is releasably attached to a complimentary parallel edge 33*a* of a second ampoule along perforated line 34 where joined. Several ampoules can be connected edge-to-edge to form a package of ampoules.

In a manufacturing process for filling the ampoule 10 of the present invention a multiple pack arrangement would facilitate filling as well as provide an improved and novel distribution packaging technique to fill two or more ampoules at a time as well as a method of packaging and distributing said ampoules in packages of two or more ampoules.

Figure 6:
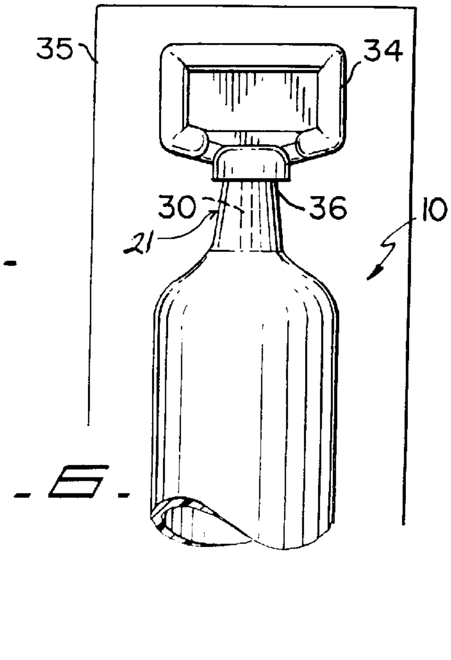
FIG. 6 is a second alternative embodiment of an ampoule without a cap assembly contained and packaged in a sterile environment.

Another alternative embodiment is shown in FIG. 6. This embodiment of FIG. 6 does not require a cover means to cover the entire tip portion 20, but only a sufficient portion of Luer Lock 21, the end 24*a* (not shown in this FIG. 6) of tip portion 20 needs to be covered. The ampoule 10 and its flag 36 are packed in a sterile environment and stored in a sterile envelope 35 (plastic or paper). When manufactured in the sterile environment, the embodiment of FIG. 6 would be placed in a sterile envelope 35 and would remain so until used. The flag 36 in this embodiment is designed to break off at neck 26 as in the prior embodiment to expose a channel passageway 30 at Luer Lock end 24*a* (not be seen in this view).

Liquid container body 11 is further constructed and arranged to be flexible and deformable such that first side 14 and second side 15 can be compressed toward each other to urge the medicinal fluid from container body 11. Preferably a single compression of said sides 14 and 15 will completely evacuate said fluid from said body 11.

In use, the ampoule 10 will be manufactured with or will later be filled with predetermined amounts of sterile medicinal fluids in a sterile environment. Ampoule 10 will be clearly labeled or coded in some manner, e.g., color coded, to indicate the contents of the ampoule. The ampoules will be distributed either singly or in packages with 2, 3 or more ampoules connected edge-to-edge as heretofore described and as shown in FIG. 4.

In venous line 23, there will be a Luer Lock connector 22 for introducing medicinal fluids into said venous line 23. In use, the breakable post 25 of ampoule 10 must be removed. This is done by twisting cap 28 or by directly bending and/or twisting breakable post 25 in order to open the sealed channel 30. Ampoule 10 is then placed in a position such that the Luer Lock connector 21 portion of ampoule 10 is aligned with the Luer Lock connector 22 of the venous line 23. The respective mating surfaces of each said Luer Lock connector 21 and 22 are placed together and said Luer Lock connector 21 and 22 are rotated to lock into place in a mated relationship. Thereafter, the sides 14 and 15 of ampoule 10 are squeezed together forcing the medicinal fluid from container body 11 through channel 30 through the Luer Lock connectors and into the venous line. Similarly, ampoule 10 can be connected to devices other than an indwelling venous line such as hypodermic needles, or other body structures to infuse the contents of ampoule 10 into the body or its structures.

Conforming to the provisions of the patent statutes, applicant has provided an explanation of the principle, preferred construction and mode of operation of this invention and has illustrated and described what is now considered to be its best embodiment. It is understood, however, that within the scope of the claimed subject matter that follows, the invention may be practiced otherwise than as specifically illustrated and described.

What is claimed is:

1. An ampoule, for dispensing medicinal fluids into a structure, said ampoule comprising:

a container for storing medicinal fluid;

said container having an end with a fluid opening initially sealed by a projection which is integral with and extends beyond said opening;

said container having a first part of a standard connector fitting at said end, for mating with a second part of a standard connector fitting of the structure; and means for breaking off said projection to terminate its sealing of said opening; whereby, upon mating of the fitting parts, fluid can be dispensed from said ampoule into the structure.

2. An ampoule according to claim 1 in which, said container has flexible walls; whereby, after said projection is broken off and the fitting parts are mated, compression of said flexible walls dispenses fluid into the structure.

3. An ampoule according to claim 2 in which, said container includes a fluid channel passing through said first connector fitting part to said end.

4. An ampoule according to claim 1 in which, said projection is in the form of a flag element which also covers said first part of said fitting; whereby, twisting of said flag element breaks it off to unseal said fluid opening and also uncover said first part of said fitting.

5. An ampoule, for dispensing medicinal fluids into a structure, said ampoule comprising:

a container for storing medicinal fluids;

said container having an end with a fluid opening sealed by a projection which extends beyond said opening;

said container having a first part of a standard connector fitting at said end, for mating with a second part of a standard connector fitting of the structure; and means for breaking off said projection to terminate its sealing of said opening;

said projection breaking off means comprising a cap which tightly engages said projection and covers said terminal end; whereby, twisting of said cap breaks off said projection, and upon mating of the fitting parts, fluid can be dispensed from said ampoule into the structure.

6. An ampoule according to claim 5 in which, said projection has a narrowed neck portion to facilitate break off upon twisting of said cap.

7. An ampoule, for dispensing medicinal fluids into a structure, said ampoule comprising:

a container for storing medicinal fluid;

at least two said ampoules connected together, side by side, in fluid isolation from each other, by detachable lateral extensions of said container;

said container having an end with a fluid opening sealed by a projection which extends beyond said opening;

said container having a first part of a standard connector fitting at said end, for mating with a second part of a standard connector fitting of the structure; and means for breaking off said projection to terminate its sealing of said opening; whereby, upon mating of the fitting parts, fluid can be dispensed from said ampoule into the structure.

8. An ampoule, for dispensing medicinal fluids into a structure, said ampoule comprising:

a container for storing medicinal fluid;

said container having an end with a fluid opening sealed by a projection which extends beyond said opening and in which said projection is in the form of a post;

said container having a first part of a standard connector fitting at said end, for mating with a second-part of a standard connector fitting of the structure; and means for breaking off said projections to terminate its sealing of said opening; whereby, bending of said post breaks off said projection and, upon mating of the fitting parts, fluid can be dispensed from said ampoule into the structure.

9. A method of dispensing medicinal fluid from an ampoule having flexible sides and a fluid opening, comprising the steps of:

storing a volume of the fluid in said ampoule;

sealing a fluid opening of said ampoule with a projection having one end integral with said opening and an opposite end extending outwardly away from said opening;

securing to said ampoule, proximate to said opening, a first part of a standard connector fitting;

breaking off said projection, at its said one end, from said ampoule for thereby;

unsealing said fluid opening of said ampoule;

mating a second part of a standard connector fitting to said first part;

squeezing said flexible sides of said ampoule; thereby dispensing said fluid from said fluid opening and through said standard connector fitting.

10. A method according to claim 9 comprising the further steps of:

covering said projection and at least a portion of said first part of said fitting with cover means; and removing said cover means to accomplish said step of breaking off said projection.

11. A method according to claim 9 in which said step of storing is of a predetermined volume and, prior to said step of mating, the additional step of:

mounting said second part of said standard connector fitting to a structure for receiving said predetermined volume as a result of said step of dispensing.

* * * * *